(12) United States Patent
Borsari

(10) Patent No.: US 10,549,058 B2
(45) Date of Patent: *Feb. 4, 2020

(54) SEAL MASK FOR THE RESPIRATORY THERAPY

(71) Applicant: DIMAR S.r.l., Medolla (IT)

(72) Inventor: Maurizio Borsari, Mirandola (IT)

(73) Assignee: DIMAR S.r.l., Medolla (IT)

( * ) Notice: Subject to any disclaimer, the term of this patent is extended or adjusted under 35 U.S.C. 154(b) by 787 days.

This patent is subject to a terminal disclaimer.

(21) Appl. No.: 15/065,154

(22) Filed: Mar. 9, 2016

(65) Prior Publication Data

US 2016/0263337 A1 Sep. 15, 2016

(30) Foreign Application Priority Data

Mar. 9, 2015 (IT) ............................... MI2015A0349

(51) Int. Cl.
*A61M 16/06* (2006.01)
*A62B 18/08* (2006.01)
(Continued)

(52) U.S. Cl.
CPC ........ *A61M 16/0616* (2014.02); *A61M 16/06* (2013.01); *A61M 16/0683* (2013.01);
(Continued)

(58) Field of Classification Search
CPC .. A61M 16/0611; A61M 16/00; A61M 16/06; A61M 16/0605; A61M 16/0616;
(Continued)

(56) References Cited

U.S. PATENT DOCUMENTS 1,112,358 A * 9/1914 Cline ....................... A42B 3/20
2/9
1,706,601 A * 3/1929 Drager ................ A62B 18/084
128/207.11
(Continued)

FOREIGN PATENT DOCUMENTS

GB        2035807 A   *  6/1980  ............. A41D 13/11
WO    WO-9720597 A1  *  6/1997  ............ A61M 16/06
(Continued)

OTHER PUBLICATIONS

Extended European Search Report dated Jul. 4, 2016 in Patent Application No. 16159236.5.
(Continued)

*Primary Examiner* — Tu A Vo
(74) *Attorney, Agent, or Firm* — Oblon, McClelland, Maier & Neustadt, L.L.P.

(57) ABSTRACT

An improved-seal mask for the respiratory therapy of the type comprising a shaped shell (12) at least covering mouth, nose and eyes of a patient (11), and provided, along a perimeter (13) which is suitable for being placed in contact against the patient's face, with a sealing gasket (14), said shaped shell (12) being provided with at least one inlet fitting (15) for the mixture of air and oxygen, said mask also comprising a neckpiece (20) provided with a plurality of prongs (21), each joined in a fixed or removable manner to a corresponding fastening point (17), distributed over the perimeter of the shaped shell (12), is provided with five fastening points (17) for the neckpiece (20), wherein two upper fastening points (17') are arranged at the height of the eyes, symmetrically with respect to a sagittal plane, two lower fastening points (17") are arranged at the height of the chin, symmetrically with respect to a sagittal plane, and a fifth fastening point (17''') is arranged centrally along an (Continued)

upper edge (18) of the mask suitable for resting on the forehead, namely in the sagittal plane.

12 Claims, 3 Drawing Sheets

(51) Int. Cl.
  *A62B 18/02* (2006.01)
  *A61M 16/04* (2006.01)
  *A61M 25/02* (2006.01)
(52) U.S. Cl.
  CPC .............. *A62B 18/02* (2013.01); *A62B 18/08* (2013.01); *A62B 18/084* (2013.01); *A61M 16/0463* (2013.01); *A61M 2025/0206* (2013.01); *A61M 2025/0213* (2013.01); *A61M 2202/0208* (2013.01); *A61M 2207/00* (2013.01); *A61M 2210/1053* (2013.01)
(58) Field of Classification Search
  CPC .......... A61M 16/0622; A61M 16/0633; A61M 16/0644; A61M 16/0641; A61M 16/0683; A61M 16/0463; A61M 2025/0206; A61M 2025/0213; A61M 2202/0208; A61M 2207/00; A61M 2210/1053; A62B 7/00; A62B 18/084; A62B 18/08; A62B 18/04; A62B 18/045; A62B 18/06; A62B 18/02; A42B 1/00; A61F 5/56; A61F 9/02; A61F 9/027
  USPC ........................................ 128/201.14, 207.17
  See application file for complete search history.

(56) References Cited

U.S. PATENT DOCUMENTS

| | | | | |
|---|---|---|---|---|
| 1,849,567 A * | 3/1932 | Christensen | ........... | A62B 18/08 128/205.27 |
| 2,156,852 A * | 5/1939 | Vaclav | ........... | A62B 18/02 128/205.27 |
| 2,199,690 A * | 5/1940 | Bullard | ........... | A62B 18/084 128/207.11 |
| 2,353,643 A * | 7/1944 | Bulbulian | ........... | A62B 18/084 128/207.11 |
| 2,381,568 A * | 8/1945 | Booharin | ........... | A62B 18/02 128/201.15 |
| 2,827,900 A * | 3/1958 | Marietta | ........... | A62B 18/02 128/206.28 |
| 3,180,333 A * | 4/1965 | Lewis | ........... | A62B 18/08 128/201.19 |
| 3,314,424 A * | 4/1967 | Berman | ........... | A62B 18/08 128/201.19 |
| 3,550,588 A * | 12/1970 | Stahl | ........... | A62B 18/08 128/201.15 |
| 3,633,575 A * | 1/1972 | Brumfield | ........... | A62B 18/02 128/206.15 |
| 4,328,797 A | 5/1982 | Rollins, III et al. | | |
| 4,595,003 A * | 6/1986 | Shoemaker | ........... | A62B 18/02 128/201.19 |
| 5,481,763 A * | 1/1996 | Brostrom | ........... | A62B 18/084 128/207.11 |
| 5,911,308 A * | 6/1999 | Chafitz | ........... | A42B 3/20 2/9 |
| 6,564,384 B1 * | 5/2003 | Kiser | ........... | A62B 18/08 2/205 |
| 7,779,832 B1 * | 8/2010 | Ho | ........... | A61M 16/0683 128/201.22 |
| 9,603,397 B2 * | 3/2017 | Symons | ........... | A61M 16/0683 |
| 2003/0213493 A1 | 11/2003 | Saad | | |
| 2004/0083534 A1 * | 5/2004 | Ruiz | ........... | A61F 5/56 2/171.2 |
| 2004/0112377 A1 * | 6/2004 | Amarasinghe | .... | A61M 16/0683 128/201.22 |
| 2006/0081252 A1 * | 4/2006 | Wood | ........... | A61M 16/0683 128/207.11 |
| 2006/0118119 A1 * | 6/2006 | Berthon-Jones | ...... | A61M 16/06 128/207.11 |
| 2006/0201514 A1 * | 9/2006 | Jones | ........... | A61M 16/06 128/206.21 |
| 2006/0283458 A1 * | 12/2006 | Woodard | ........... | A61M 16/06 128/206.24 |
| 2007/0163595 A1 * | 7/2007 | Chen | ........... | A41D 13/1161 128/207.11 |
| 2008/0072910 A1 * | 3/2008 | Janbakhsh | ........... | A61M 16/06 128/206.27 |
| 2008/0115788 A1 * | 5/2008 | Eschen | ........... | A62B 18/084 128/207.11 |
| 2008/0178875 A1 * | 7/2008 | Henry | ........... | A61M 16/06 128/201.22 |
| 2008/0264422 A1 * | 10/2008 | Fishman | ........... | A61M 16/06 128/207.11 |
| 2009/0038622 A1 * | 2/2009 | Amarasinghe | .... | A61M 16/0683 128/207.17 |
| 2010/0258131 A1 | 10/2010 | Gaffney et al. | | |
| 2010/0258133 A1 | 10/2010 | Todd et al. | | |
| 2011/0197341 A1 | 8/2011 | Formica et al. | | |
| 2011/0297157 A1 | 12/2011 | Wallnewitz | | |
| 2012/0094806 A1 * | 4/2012 | Danford | ........... | A63B 21/0004 482/13 |
| 2014/0034057 A1 | 2/2014 | Todd et al. | | |
| 2014/0096774 A1 * | 4/2014 | Olsen | ........... | A61M 16/06 128/205.25 |
| 2015/0128953 A1 | 5/2015 | Formica et al. | | |

FOREIGN PATENT DOCUMENTS

| | | | | |
|---|---|---|---|---|
| WO | WO-9803225 A1 * | 1/1998 | ............ | A62B 18/08 |
| WO | WO 2009/063402 A1 | 5/2009 | | |
| WO | WO 2010/066004 A1 | 6/2010 | | |

OTHER PUBLICATIONS

Italian Search Report dated Jul. 14, 2015 in Italian Application MI20150349, filed on Mar. 9, 2015 (with English Translation of Categories of Cited Documents).

* cited by examiner

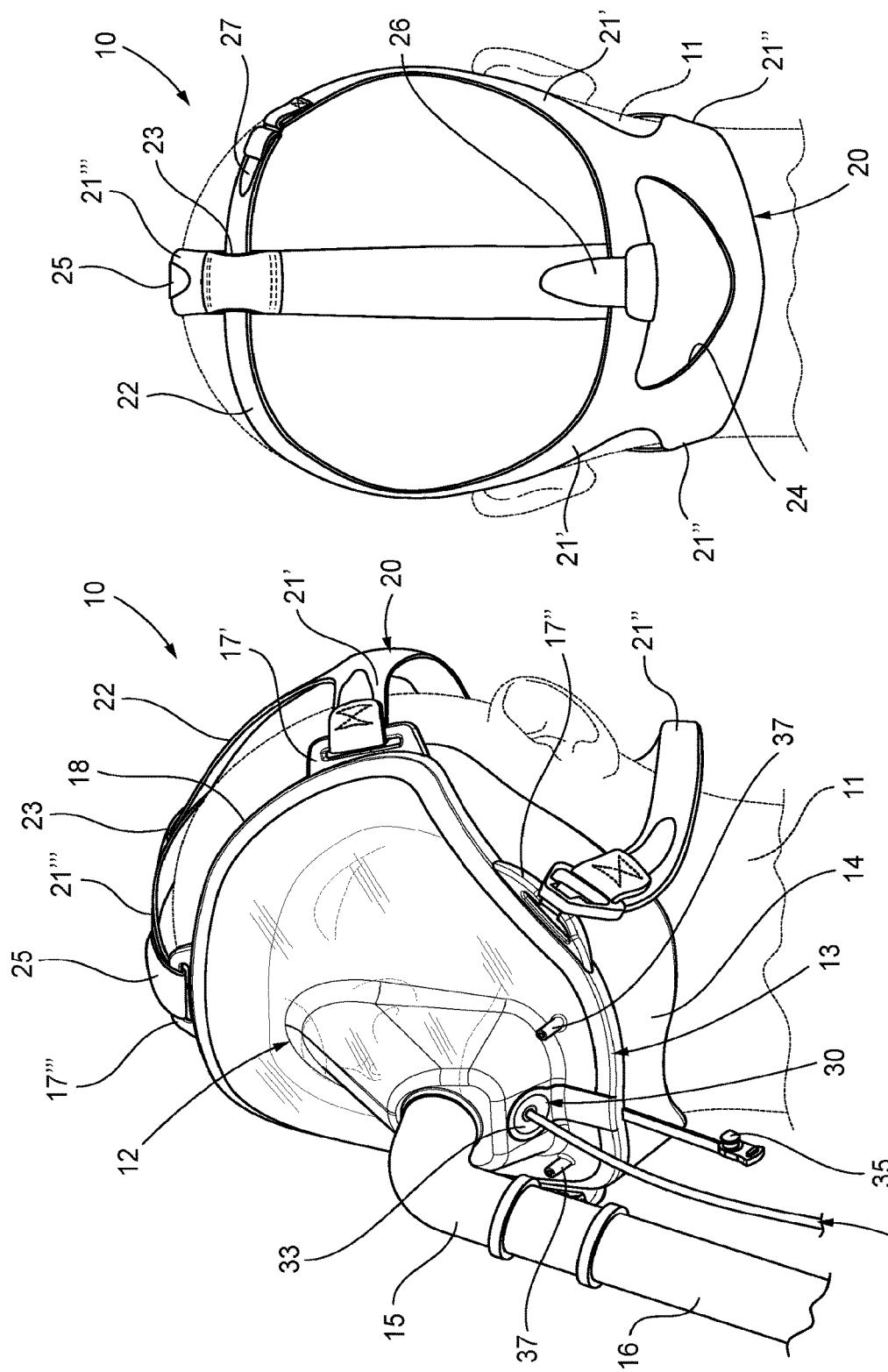

SEAL MASK FOR THE RESPIRATORY THERAPY

The present invention refers to an improved-seal mask for the respiratory therapy.

Masks for the administration of a respiratory therapy to a patient in home or hospital environment are known, which can be divided into: nasal masks, covering just the nose, oral-nasal masks, also called facial and covering nose and mouth, and total face masks, also called "total face", covering the entire face and therefore also the eye area.

The masks comprise a rigid shell made of plastic material, three-dimensionally shaped in order to receive the patient's face, provided with a sealing gasket made of elastomeric material along the entire perimeter to be drawn near the patient's face. Furthermore, the rigid shell comprises an inlet fitting for inletting the mixture of air and oxygen coming from a ventilation apparatus and fastening points of fixing means for fixing the mask to the patient's head, constituted by a so-called neckpiece that maintains the mask on the patient's head as much stably and closely as possible.

The masks for the respiratory therapy known nowadays have four fastening points for fastening the neckpiece, two of which are respectively placed at the height of the eyes, symmetrically with respect to a sagittal plane, which two opposite upper prongs of the neckpiece passing above the ears are connected to, and the other two are placed at the height of the chin symmetrically with respect to a sagittal plane, which two opposite lower prongs passing below the ears are connected to.

The main critical aspect of the masks for the administration of a respiratory therapy to a patient in home or hospital environment, regards the pneumatic seal between the gasket and the patient's face.

This problem is emphasized by the fact that such masks are subject to an internal positive pressure and should ideally be worn for medium-long time intervals. In fact, patients suffering from acute respiratory insufficiency, namely those who are not able to draw air through own inspiration, or anyway must avoid such an inspiration effort, are supported through the mask with a positive pressure that pushes the mixture of air and oxygen into the lungs. Precisely because the mask is in positive pressure, it is absolutely necessary to ensure a pneumatic seal, failing which the loss of pressure, which results in a dangerous loss of therapeutic efficacy.

In order to ensure the pneumatic seal of the positive pressure to the patient's face, the masks provided with four fastening points are forcefully pulled and fastened to the patient's face through the four prongs of the neckpiece.

This causes an initial phase of discomfort and claustrophobia to the patient that, over time, turns into pain up to the formation of decubitus sores (compression of the skin tissue with obstruction of blood vascularisation), thus limiting its use to few hours, generally 6-20 hours.

The quality of the mask seal on the patient's face, which is so important for the success of the therapy, depends on several factors, among which the most important are:
  anatomy and morphology of the patient's face;
  weight, volume and mask encumbrance;
  weight and length of the breathing circuit connected to the mask.

In fact, for example, the weight of the tubes and of the relative accessories, such as filters, nebulizers, etc., that connect the masks to the ventilation apparatuses, generates a lever with fulcrum on the patient's face that tends to detach the mask from the forehead making it rotate downwards, a movement that is accentuated by the respiratory cycle of the patient that raises and lowers the system at each respiratory cycle. The part of the mask that is mainly affected by this situation is that of the frontal support, with the consequence of accentuating the pressure losses between the supporting gasket of the mask and patient's forehead. The loss of pressure reduces the therapy effectiveness up to its failure, which determines the necessity of intubation and related consequences. In order to try to counteract such a phenomenon, it is now only possible to strongly tighten the mask on the patient's face by pulling more strongly the four fastening prongs of the neckpiece with the above mentioned drawbacks for the patient, such as discomfort, decubitus sores, ulcers, etc.

A further serious consequence of the pneumatic losses in masks for the administration of a respiratory therapy consists of the so-called "dyssynchrony" between the patient and the ventilation apparatus, namely the lack of synchronism between the respiratory needs of the patient and the response of the ventilation apparatus. In fact, when the patient draws air, by inhaling inside the machine, the ventilation apparatus perceives this air request, which actually consists of a pressure drop inside the mask itself.

Due to the losses from the mask, the ventilation apparatus interprets the pressure drop as an air request—inspiratory act—by the patient, supplying the gaseous mixture, usually formed by air and oxygen, to the mask. Actually, as the pressure drop is caused by the loss and not by the inspiratory act of the patient, the ventilation apparatus supplies air even if the patient is still in the expiratory phase or in the pause between the end of an expiratory act and the beginning of the following. The consequence is the mentioned dyssynchrony that implies, as well understandable, a serious respiratory discomfort for the patient up to the failure of the therapy.

Another drawback of the seal in known oral-nasal masks derives from the frequent use, by patients undergoing respiratory therapy due to hypoxemic or acute respiratory insufficiency, of a nasogastric tube for feeding, eliminating air in the stomach caused by the pressure of the ventilation apparatus, etc.. The nasogastric tube is placed inside the stomach of the patient passing through a nostril and must be connected to the appropriate collecting systems dedicated to it.

Therefore, it must be directed outwards the respiratory mask, but the passage through the common fittings present in the respiratory masks is not possible, as the nasogastric tube has a very big conical distal connector that connects it to the apparatus and the small proximal end is already inserted in the patient.

The only solution currently applied consists in making the nasogastric tube, of about 4-8 mm diameter, pass under the pneumatic sealing gasket of the mask, usually on the patient's cheek, between membrane and skin.

Obviously, in this case a loss of pressure and/or flow is generated, which causes all the above mentioned problems. In order to avoid this loss, the personnel in charge tends to pull even more the neckpiece, pressing the portion of the tube involved on the cheek of the patient, in order to try to reduce the losses by exploiting the elasticity and softness of the skin in that point.

However, this causes a discomfort for the patient with the risk of contact decubitus sores and/or ulcers, increase in pain and the consequent early interruption, if not the failure of the respiratory therapy.

The aim of the present invention is to make an improved-seal mask for the respiratory therapy that solves the above mentioned drawbacks.

Another aim of the present invention is to make an improved-seal mask for the respiratory therapy, which, through a reduced compression to the patient's face, allows a continuatively and prolonged use that can last days without decubitus sores, losses or other therapeutic problems.

A further aim of the present invention is to make an improved-seal mask for respiratory therapy that optimizes the respiratory therapy by ensuring the synchronism between the patient and the ventilation apparatus.

Another aim of the present invention is to make an improved-seal mask for the respiratory therapy particularly simple and functional, as well as cost-effective.

These aims according to the present invention are achieved by making an improved-seal mask for the respiratory therapy as outlined in claim 1.

Further features are provided in the dependent claims.

The features and advantages of an improved-seal mask for the respiratory therapy according to the present invention will become clearer from the following exemplary and non-limiting description, referred to the enclosed schematic drawings in which:

FIGS. 1A and 1B show an improved-seal mask for the respiratory therapy according to the invention worn by a patient, wherein in FIG. 1A, for greater clarity of representation, the mask is shown with the neckpiece bands in a loose position prior to their tensioning on the head;

Figure 3:
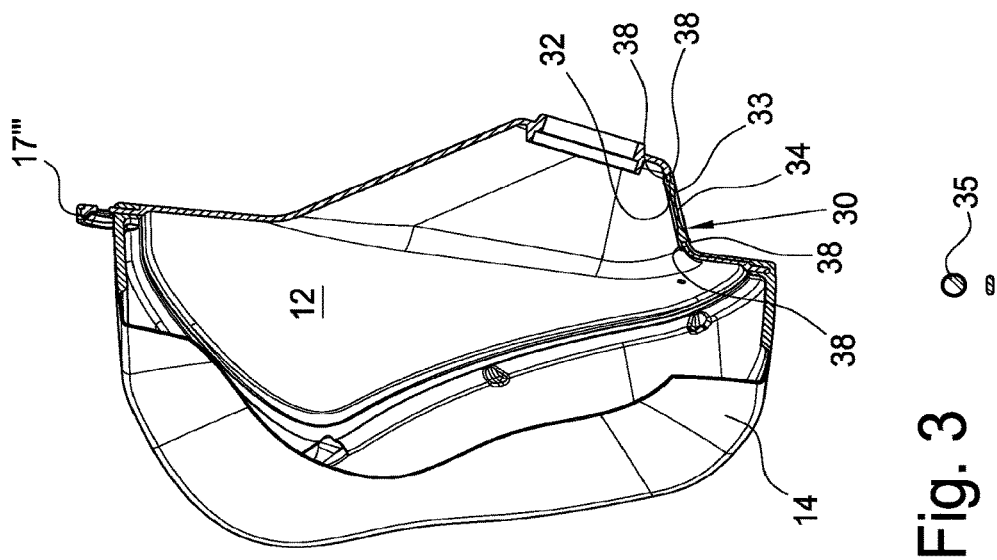
FIG. 3 is a section of the shaped shell of FIG. 2 along the track plane III-III.
Figure 2:
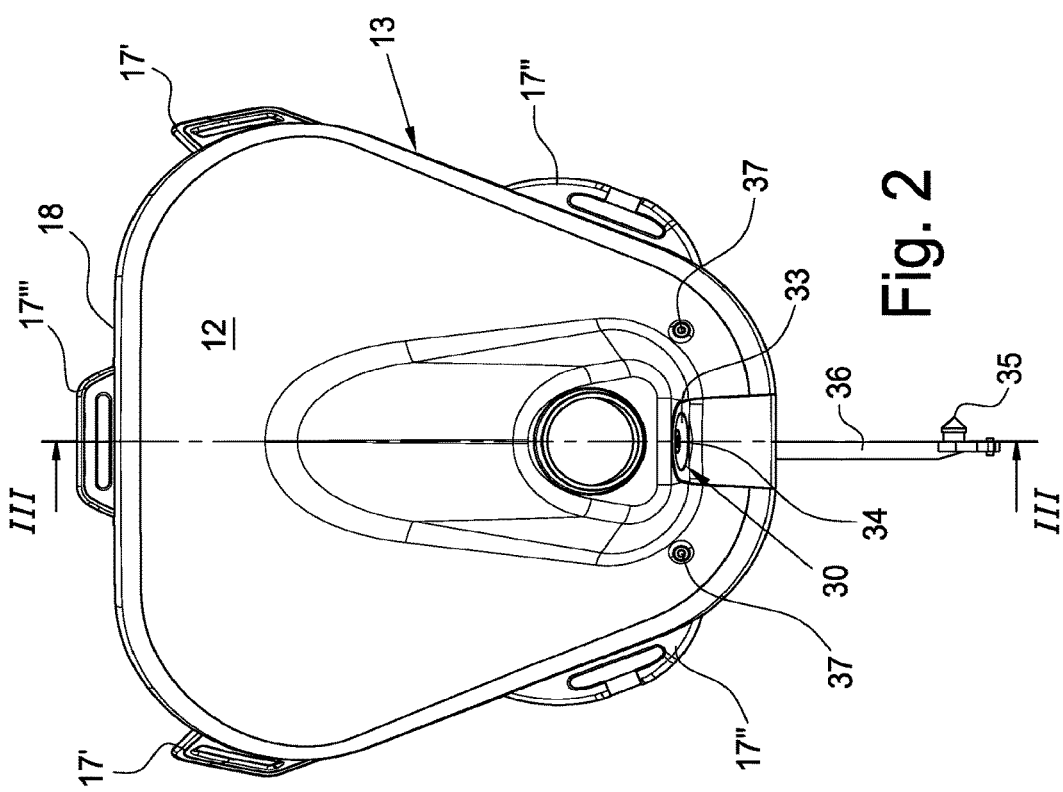
FIG. 2 is a front elevation view of the shaped shell of the mask according to the invention.
Figure 5:
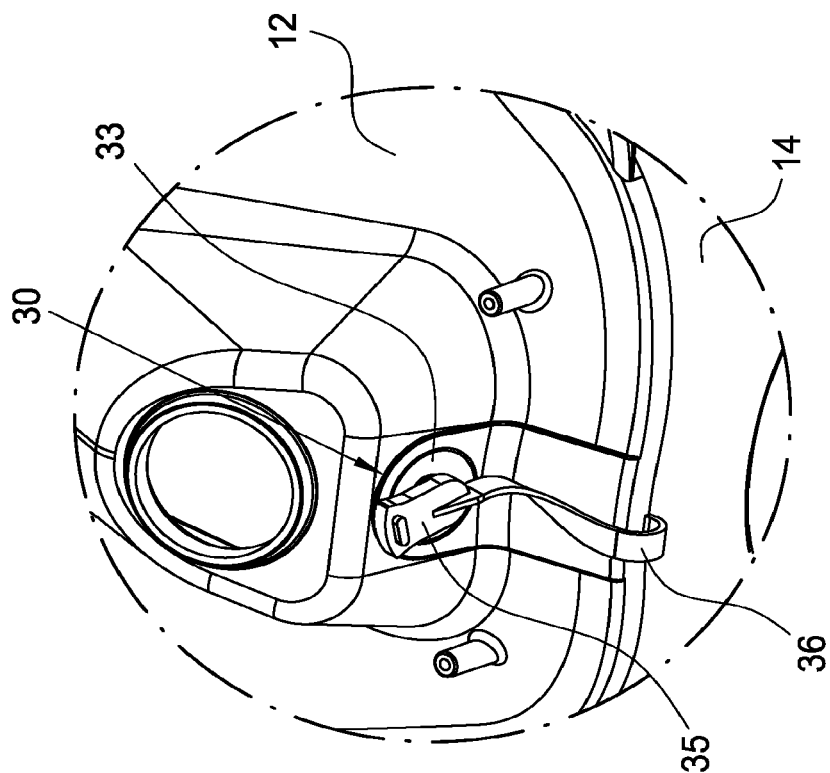
FIGS. 4 and 5 show, through an enlarged detail, a dedicated access for a nasogastric tube according to a particular embodiment of the invention, respectively with the closing plug in the closed position and in the open position.
Figure 4:
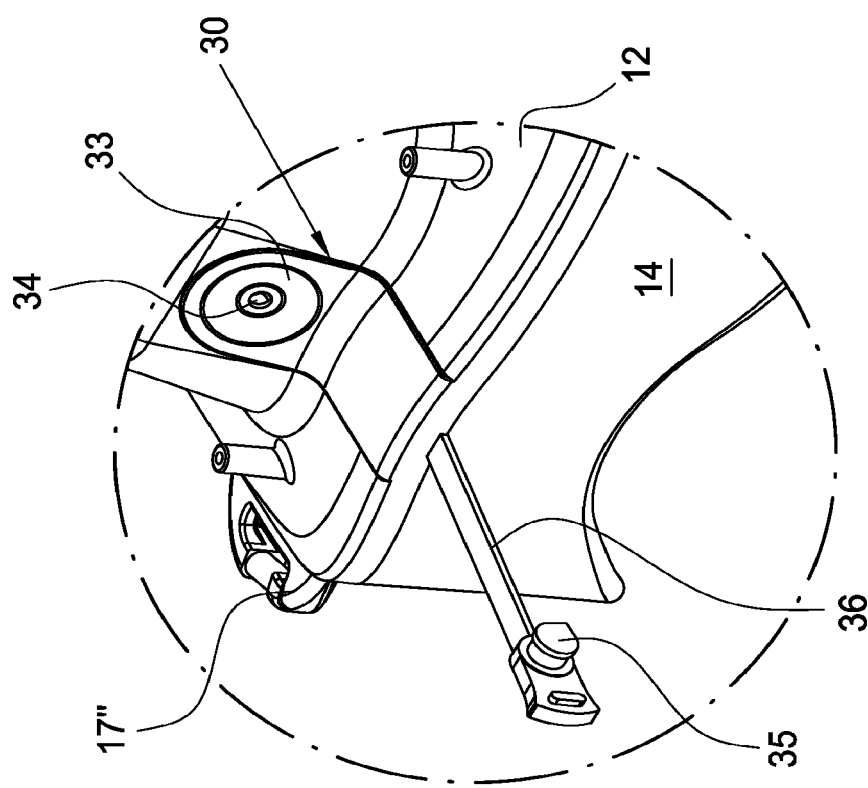

With reference to the figures, an improved-seal mask for the respiratory therapy is shown, wholly indicated with reference number 10, and comprising a shaped shell 12 at least covering the mouth, nose and eyes of a patient 11. The shaped shell 12 is provided with a sealing gasket 14 along a perimeter 13, suitable for being placed in contact against the patient's face 11.

The mask 10 according to the invention is made of the rigid shaped shell 12 of polycarbonate (PC) or copolyester (PETG) and of the gasket 14, preferably overmoulded, of thermoplastic elastomer (TPE).

The making of the gasket 14 as an enbloc with the shaped shell 12 first of all allows eliminating the manual assemblies of the rigid part with the soft one and, furthermore, having a gasket 14 with a continuous profile with respect to the shaped shell 13, so as to eliminate any gap or recess that make the cleaning difficult.

The shaped shell 12 is provided with at least one inlet fitting 15 for inletting the mixture of air and oxygen coming from a ventilation apparatus, not shown, through a tube 16. The inlet fitting 15 can be of any known type, for example of the so-called "vented" or "not vented" type, that is provided or not provided with a free-passage hole for the exit of carbon dioxide expired by the patient outwardly.

The mask 10 according to the invention comprises a neckpiece 20, provided with a plurality of prongs 21, each joined in a fixed or removable manner to a corresponding fastening point 17 placed on the perimeter 13 of the shaped shell 12. It deals with a band system wrapping the rear side, or nape, of the patient 11, through which it is firmly fixed the mask 10 on the patient's face in order to obtain a pneumatic seal of the gasket 14 on the face.

According to one embodiment of the invention, the shaped shell 12 comprises five fastening points 17 for fastening the neckpiece 20, wherein two upper fastening points 17' are placed at the height of the eyes symmetrically with respect to a sagittal plane, two lower fastening points 17" are placed at the height of the chin, symmetrically with respect to a sagittal plane, and a fifth fastening point 17''' is placed centrally along an upper edge 18 of the mask, namely it is in the sagittal plane.

The neckpiece 20, according to the invention, comprises two opposite upper prongs 21' of adjustable length, suitable for passing over the ears, two opposite lower prongs 21" of adjustable length suitable for passing under the ears, and a central prong 21''', suitable for being arranged on the head in the sagittal plane.

Retaining the mask 10 through the fifth prong 21''' in contact with the forehead also in the central part, the rotation effect downwards of the mask that would cause the detachment of the sealing gasket 14 from the forehead is avoided, thus generating in turn pneumatic leaks between forehead and mask.

The neckpiece 20, shown in FIGS. 1A and 1B as an example, comprises a connection band 22 between the two opposite upper prongs 21', having an end 27 of adjustable length, and suitable for arranging on the upper part of the head. The central prong 21''' is inserted onto the connection band 22 by a through-ring 23, or slot, that must allow the transversal sliding, on the right or on the left of the central prong 21''' on the connection band 22 in order to be able to centre the same in the sagittal plane on the top of the head. The central prong 21''' is constrained in an adjustable manner in length in the sagittal plane to both ends 25 and 26, in particular at the front end 25 it is constrained to the perimeter 13 of the shaped shell 12 and at the rear end 24 it is constrained to a central portion of convergence 24 of the opposite upper prongs 21' and lower prongs 21". In the example shown for illustrative and not-limiting purpose, the ends 25 adjustable in length, as well as 26 and 27 respectively of the connection band 22 and of the central prong 21''' are made through transmission in a ring and the closure through Velcro®.

The three adjustments of the central prong 21''', namely in length in the sagittal plane at both ends 25 and 26 and transversally with respect to the connection band 22, allow having, for any patient head size, a correct placement of the central prong 21''' in the sagittal plane and of the connection band 22 on the top of the head for a correct distribution of the forces.

According to a further aspect of the present invention, the mask 10 for the respiratory therapy comprises a dedicated access 30 for a nasogastric tube 31. On the shaped shell 12, close to the nostrils, a hole 32 is made having dimensions of about 20 mm, namely dimensions sufficient for the passage of the distal end of the nasogastric tube. On the hole 32 an elastic membrane 33 is stably applied, which is provided with an expandable hole 34 and with a closure plug 35 for such a hole. The elastic membrane 33, of circular shape in the example, is made as an enbloc with the shaped shell 12 by overmoulding a thermoplastic elastomer (TPE). In this manner the elastic membrane 33 is an integral and indissoluble part of the shaped shell 12 of the mask itself and does not risk to be separated therefrom due to the positive pressure inside the mask.

In the example shown, the elastic membrane 33 has a section having decreasing thickness towards the hole 34, in order to allow a higher dilatability of the hole 34.

Furthermore, the elastic membrane 33 circumferentially has, in the connection portion with the hole 32 of the shaped shell 12, two opposite annular lips 38, each respectively resting inside and outside the shaped shell 12. Such arrangement ensures, in addition to the bonding by fusion obtained through the overmoulding, that the elastic membrane 33 overmoulded on the shaped shell 12 stably remains in position even if subject to relatively high positive internal pressures and does not risk to accidentally exit from its seat.

The expandable hole 34, according to a non-limiting embodiment, has at rest a diameter of about 3 mm, namely slightly less than the diameter of the small tube of the nasogastric tube 31, so as to make a pneumatic seal by interference on the small tube of the nasogastric tube 31 when this is in position.

According to a further embodiment, not shown, the expandable hole 34 could also be provided with a split in order to enlarge it more, for the insertion of the nasogastric tube 31.

When the use of a nasogastric tube is necessary, its distal end is inserted through the expandable hole 34 of the elastic membrane 33, that closes around the small tube of the nasogastric tube 31 to ensure the pneumatic seal of the mask 10.

The closure plug 35, that for the sake of simplicity in making the piece can also be made as an enbloc with the shaped shell 12 through overmoulding, is shown at the end of a stem 36 and is useful to seal close the expandable hole 34 when the nasogastric tube 31 is not used.

According to a particular embodiment that makes the mould construction and the injection modes of the materials into the mould easier, as shown in the figures, the sealing gasket 14, the perforated elastic membrane 33 and the related closure plug 35 at the end of the stem 36 are made without solution of continuity through a unique injection point for injecting the thermoplastic material into the mould.

According to an embodiment shown as an example, the mask according to the invention is also provided with a pair of so-called "luer cones" 37, namely two small perforated channels that constitute exhalation holes, namely outlet holes for outletting the gas exhaled by the patient, as well as with the medical standard connection, for the connection with possible manometers or other medical devices.

The several embodiments of the mask according to the invention, and in particular the making of the fifth fastening point and of a dedicated access for the nasogastric tube, can contribute along with a synergistic effect of a significant improvement of the pneumatic seal or can form features independent from each other.

The improved-seal mask for the respiratory therapy subject-matter of the present invention has the advantage of allowing, thanks to the insertion of the fifth fastening point, a better uniform distribution of the contact pressure, by pulling less the mask on the patient's face and avoiding the compression that generates decubitus points.

By inserting the fifth fastening point, in addition to better distributing the contact pressure with the patient's face, with a great reduction of losses in all of the contact points of the mask with the face, the mask is prevented from rotating downwards, with the consequent detachment from the forehead and therapeutic pressure losses.

Furthermore, it has been observed that the possibility to distribute the traction load of the neckpiece of the mask in more points greatly reduces the contact pressure, as the total force to be exerted is proportionally reduced more than the sole distribution on an additional point.

Advantageously, the mask allows a higher comfort for the patient with a lower risk of decubitus and/or ulcer that will allow the patient to wear it for longer periods of time, namely also for respiratory treatments beyond 24 hours.

The best pneumatic seal advantageously allows the significant improvement of the therapy also from the synchronism point of view between the patient and the ventilation apparatus.

Furthermore, the particular solution proposed also allows creating a pneumatic seal passage dedicated to the nasogastric tube passage, without problems of pressures losses and/or flow and/or decubitus and all the deriving negative consequences, already listed above.

The improved-seal mask for the respiratory therapy thus conceived can be subject to numerous modifications and variants, all falling within the invention; moreover, all the details are replaceable by technically equivalent elements. In practice, the materials used, as well as the dimensions, can be any according to the technical needs.

The invention claimed is:

1. A mask for respiratory therapy comprising:
a shaped shell configured to at least covering a mouth, a nose and eyes of a patient and including:
a sealing gasket, along a perimeter which is suitable for being placed in contact against the patient's face,
at least one inlet fitting for mixing air and oxygen
five fastening points distributed over the perimeter of said shaped shell, wherein the five fastening points, include (a) two upper fastening points arranged at a height of the eyes, symmetrically with respect to a sagittal plane, (b) two lower fastening points arranged at a height of the chin, symmetrically with respect to a sagittal plane, and (c) a fifth fastening point arranged centrally in the sagittal plane along an upper edge of the mask suitable for resting on a forehead of the patient; and
a neckpiece including five prongs, each joined in a fixed or removable manner to a corresponding fastening point of the five fastening points, wherein the five prongs include (a) two opposite upper prongs suitable for passing over ears of the patient, (b) two opposite lower prongs suitable for passing under the ears, and (c) a central prong suitable for being arranged on a head of the patient centrally in the sagittal plane, said central prong being adjustable in length at both a front end and at a rear end, and the neckpiece comprises an upper intermediate band connecting the two opposite upper prongs, a lower intermediate band connecting the two opposite lower prongs, and two opposite intermediate bands positioned between the two opposite upper prongs and the two opposite lower prongs, wherein an opening is formed by the upper intermediate band, the lower intermediate band, and the two opposite intermediate bands, and said neckpiece comprises an adjustable length connection band that is positioned above the opening and between two opposite upper prongs, said central prong is connected to the upper intermediate band, and the central prong is being inserted through said adjustable length connection band through a through-ring that allows transversal sliding of said central prong on said adjustable length connection band for centering in the sagittal plane on a top of the head.

2. The mask according to claim 1, wherein said sealing gasket is made through overmoulding as an enbloc with said shaped shell.

3. The mask according to claim 2, wherein said shaped shell is a rigid shell made from polycarbonate (PC) and said sealing gasket is made from thermoplastic elastomer (TPE).

4. The mask according to claim 2, wherein said shaped shell is a rigid shell made from copolyester (PETG) and said sealing gasket is made from thermoplastic elastomer (TPE).

5. The mask according to claim 1, further comprising a pneumatic-sealed dedicated access for a nasogastric tube, wherein said shaped shell bears a hole having sufficient dimensions for passing an end of the nasogastric tube.

6. The mask according to claim 5, further comprising an elastic membrane applied to said hole of said shaped shell, said elastic membrane being equipped with an expandable hole and with a closing plug, said expandable hole having a diameter suitable for making a pneumatic seal on a small tube of the nasogastric tube when in position.

7. The mask according to claim 6, wherein said elastic membrane is made as an enbloc with said shaped shell through overmoulding of a thermoplastic elastomer (TPE) on said shaped shell, wherein said shaped shell is made from polycarbonate (PC).

8. The mask according to claim 7, wherein said elastic membrane has, circumferentially, in a connection portion with said hole of said shaped shell, two opposite annular lips, each respectively resting inside and outside said shaped shell.

9. The mask according to claim 8, wherein said sealing gasket, said elastic membrane, and said closing plug are made without solution of continuity through a single injection point for injecting the thermoplastic elastomer into a mould.

10. The mask according to claim 6, wherein said elastic membrane is made with said shaped shell through overmoulding of a thermoplastic elastomer (TPE) on said shaped shell.

11. The mask according to claim 6, wherein said elastic membrane is made as an enbloc with said shaped shell through overmoulding of a thermoplastic elastomer (TPE) on said shaped shell, wherein said shaped shell is made from copolyester (PETG).

12. The mask according to claim 1, wherein said sealing gasket is made through overmoulding with said shaped shell.

* * * * *